United States Patent [19]

König et al.

[11] Patent Number: 4,888,125

[45] Date of Patent: Dec. 19, 1989

[54] DIISOCYANATES, A PROCESS FOR THEIR PRODUCTION AND THEIR USE IN THE PRODUCTION OF POLYURETHANE PLASTICS

[75] Inventors: Klaus König, Odenthal; Peter Heitkämper, Dormagen, both of Fed. Rep. of Germany

[73] Assignee: Bayer Aktiengesellschaft, Bayerwerk, Fed. Rep. of Germany

[21] Appl. No.: 128,295

[22] Filed: Dec. 3, 1987

[30] Foreign Application Priority Data

Dec. 6, 1986 [DE] Fed. Rep. of Germany ....... 3641702

[51] Int. Cl.$^4$ .................... C07C 118/00; C08G 18/00
[52] U.S. Cl. ................. 252/182.21; 560/338; 560/339; 560/359
[58] Field of Search ................. 560/358, 359

[56] References Cited

U.S. PATENT DOCUMENTS

| 3,555,071 | 1/1971 | Rao et al. | 560/358 |
| 3,704,307 | 11/1972 | Zecher et al. | 560/358 |
| 4,421,870 | 12/1983 | Stutz et al. | 521/160 |
| 4,448,946 | 5/1984 | Stutz et al. | 528/67 |
| 4,597,910 | 7/1986 | König et al. | 560/359 |

FOREIGN PATENT DOCUMENTS

| 1146957 | 5/1983 | Canada | 560/359 |
| 3442689 | 5/1986 | Fed. Rep. of Germany | 560/359 |

OTHER PUBLICATIONS

Justus Liebigs, Annalen der Chemie, No. 562, 1949, p. 129.
Journal of American Chemical Society, No. 74, 1952, p. 5230.
Kunststoff Handbuch, Polyurethane, vol. 7, 2nd Edition, 1983.

*Primary Examiner*—Harold D. Anderson
*Assistant Examiner*—Dennis R. Daley
*Attorney, Agent, or Firm*—Joseph C. Gil; Richard E. L. Henderson

[57] ABSTRACT

α-(4-isocyanatophenoxy)-ψ-(4-isocyanato-3-methylphenoxy)-alkanes and mixtures thereof with the corresponding methyl-free and/or dimethyl substituted diisocyanates are made by phosgenating the corresponding diamine(s). These diisocyanates do not form a precipitate when reacted with a polyol and produce polyurethanes having outstanding properties.

4 Claims, No Drawings

DIISOCYANATES, A PROCESS FOR THEIR PRODUCTION AND THEIR USE IN THE PRODUCTION OF POLYURETHANE PLASTICS

BACKGROUND OF THE INVENTION

This invention relates to α-4-isocyanatophenoxy)-ω-(4-isocyanato-3-methylphenoxy)-alkanes and mixtures thereof with the corresponding diisocyanates free from methyl substituents and the corresponding symmetrically di-methyl-substituted diisocyanates, to a process for producing these diisocyanates and diisocyanate mixtures and to their use as synthesis component(s) in the production of polyurethane plastics.

The properties of a polyurethane plastic, particularly polyurethane elastomer, are largely determined by the nature of the polyisocyanate used in the production of the plastic. Thus, particularly high-quality polyurethane elastomers are obtained, for example, where 1,5-diisocyanatonaphthalene is used as the diisocyanate component. In particular, cast elastomers based on this diisocyanate are distinguished by excellent mechanical properties (See for example Becker, Braun, Kunststoff-Handbuch, Vol. 7, 2nd Edition (1983), Carl-Hanser-Verlag). However, 1,5-diisocyanatonaphthalene is attended by the disadvantages that the raw material required for its production, namely naphthalene, is only available in limited quantities. In addition, the nitration of naphthalene leads inevitably to an isomer mixture of nitronaphthalenes from which 1, 5-dinitronaphthalene has to be isolated. Purification by distillation of the 1,5-diisocyanatonaphthalene obtained from the dinitro compound by hydrogenation and subsequent phosgenation of the resulting diamine also involves difficulties because it tends to sublime. The net result of this is that 1,5-diisocyanatonaphthalene is expensive to produce.

The processing of 1,5-diisocyanatonaphthalene is also difficult in many cases because its melting point and its vapor pressure are relatively high. These properties often make it impossible for 1,5-diisocyanatonaphthalene to be readily reacted in the form of a melt. Technically elaborate processing methods and protective measures are thus necessary to avoid chemical and industrial hygiene problems.

Accordingly, there has been no shortage of attempts to find an equivalent replacement for 1,5-diisocyanatonaphthalene as diisocyanate component in the production of high-quality polyurethane plastics.

DE-OS 3,138,421 and DE-OS 3,138,422, for example describe the production of polyurethane elastomers using 4, 4'-diisocyanato-1, 2-diphenylethane as the diisocyanate component. Although plastics showing favorable mechanical properties can be obtained with this diisocyanate, the production of 4, 4'-diisocyanato1, 2-diphenylethane is complicated and expensive and, hitherto, has always been difficult to achieve on an industrial scale.

Numerous attempts have also been made to use the comparatively inexpensive 4, 4'-diisocyanatodiphenylmethane instead of 1, 5-diisocyanatonaphthalene for the production of high-quality polyurethane elastomers. However, until now, all attempts to produce polyurethane elastomers based on this diisocyanate which correspond in their mechanical and thermal properties to polyurethane elastomers based on 1,5-diisocyanatonaphthalene have always ended in failure.

α, ω-bis-(4-isocyanatophenoxy)-ethane,-n-butane and-n-hexane are described in DE-OS 3,442,689 as synthesis components for polyurethane plastics. Although the use of these diisocyanates in polyurethane elastomers does give products having outstanding properties, difficulties are sometimes encountered in the processing of these isocyanates. These diisocyanates do give the desired reaction products containing highly crystalline rigid segments but they are highly reactive. Consequently, when these diisocyanates are reacted with polyols, solids can precipitate spontaneously from the liquid reaction mixtures. Such precipitation affects the industrial application of reactions of the type in question, particularly for the production of prepolymers.

Accordingly, there is an interest in diisocyanates having the same basic structure, but reduced reactivity. A first step in this direction can be seen in the diisocyanates according to DE-OS 3,525,606 (EP-A-0,183,115). The α,ω-bis-(4-isocyanato-3-methylphenoxy)-alkanes described in this publication do not present any difficulties by precipitation of solids in their reaction with polyols and the polyurethane plastics obtained also show a range of outstanding properties. However, the disadvantage of these diisocyanates is that their reactivity is unexpectedly reduced severely by the two methyl substituents. Consequently, the reaction of these isocyanates with polyols generally requires the addition of catalyst. This can be unfavorable, particularly in the production of prepolymers.

SUMMARY OF THE INVENTION

It is an object of the present invention to provide new diisocyanates and diisocyanate mixtures which are comparable with 1,5-diisocyanatonaphthalene in their suitability for the production of high-quality polyurethane elastomers and which are not attended by the disadvantages of the state-of-the-art diisocyanates mentioned above.

This and other objects which will be apparent to those skilled in the art are achieved by the provisions of the diisocyanates and diisocyanate mixtures corresponding to specified formula(e) which are described in detail hereinafter by phosgenating the corresponding amine(s).

DETAILED DESCRIPTION OF THE INVENTION

The present invention relates to diisocyanates or diisocyanate mixtures which are characterized in that (a) from 30 to 100 wt. % of diisocyanate(s) corresponding to the general formula

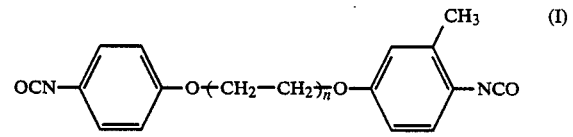

(b) from 0 to 50 wt. % of diisocyanate(s) corresponding to the general formula

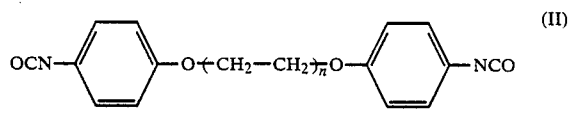

and (c) from 0 to 50 wt. % of diisocyanate(s) corresponding
to the general formula

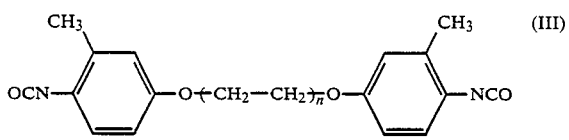

"n" in each of these formulae may have a value of 1, 2 or 3. The percentages indicated add up to 100 wt. %.

The diisocyanate(s) and diisocyanate mixtures of the present invention are not only superior in their processibility to the diisocyanates disclosed in DE-OS 3,442,689 and EP-A-0,183,115, they are also much more suitable for the production of high-quality polyurethane elastomers than the 1, 2-bis-(2-isocyanatophenoxy)-ethane described in "Annalen der Chemie", 562 (1949), page 129, and the 1, 3-bis-(4-isocyanatophenoxy)-propane described in "Journal of the American Chemical Society", 74 (1952), page 5230.

The present invention also relates to a process for the production of the diisocyanates and diisocyanate mixtures described above in which (a) diamine(s) corresponding to the general formula

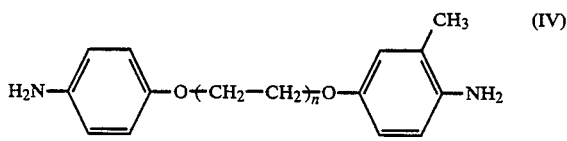

or mixtures of these diamines with (b) diamine(s) corresponding to the general formula

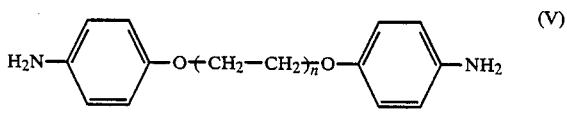

and with (c) diamine(s) corresponding to the general formula

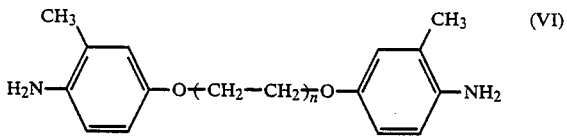

or adducts thereof with hydrogen chloride or carbon dioxide are reacted in known manner with phosgene. "n" in each of the above formulae may be 1, 2 or 3 and the quantitative composition of the diamine mixtures optionally used must be such that diisocyanate mixtures satisfying the quantitative limitations for mixtures within the scope of the present invention are obtained.

The present invention also relates to the use of the diisocyanates or diisocyanate mixtures of the present invention as a synthesis component in the production of polyurethane plastics by the isocyanate polyaddition process.

The diamines used in the phosgenation process of the present invention, which correspond to the following general formula

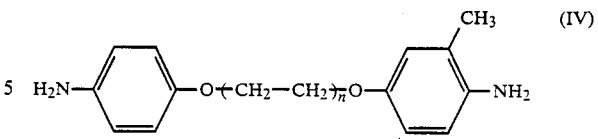

may be advantageously prepared from the corresponding α-(4-nitrophenoxy)-ω-(4-nitro-3-methylphenoxy)-alkanes by reduction with base metals (for example, tin or iron) in the presence of acids or by catalytic hydrogenation. The diamines may of course also be prepared by any other method known to those in the art.

The dinitro compounds on which the diamines are based may be prepared, for example, by two-stage condensation in accordance with the prior art (See, for example, "The Chemistry of the Ether Linkage", Ed. S. Patai, Interscience Publishers, 1967, pages 445 to 498). For illustrative purposes, several possible methods for the synthesis of 1-(4-nitrophenoxy)-2-(4-nitro-3-methylphenoxy)-ethane are described below.

The condensation of 2-chloroethanol with alkali-4-nitrophenolate in a first step gives 2-(4-nitrophenoxy)-ethanol which may also be obtained by reaction of 4-nitrophenol with ethylene oxide or with glycol carbonate (See, Houben-Weyl, Methoden der Organischen Chemie, Vol. 6/3, Georg Thieme Verlag, 1965, page 75). 2-(4-nitrophenoxy)-ethanol may then be reacted in a second step with 2-nitro-5-chlorotoluene in the presence of bases to form the desired product. In another possible synthesis method, 2-(4-nitrophenoxy)ethanol is reacted with 4-toluene sulfonic acid chloride to form the corresponding sulfonic acid ester which may then be reacted with 4-nitro-3-methylphenol to form the required dinitro compound (See Houben-Weyl, Methoden der Organischen Chemie, Vol. 6/3, Georg Thieme Verlag, 1965, pages 68 and 69).

It is also possible to reverse the order and initially prepare 2-(4-nitro-3-methylphenoxy)-ethanol from which the desired compound may then be obtained either by reaction with 4-nitrochlorobenzene or, after esterification with 4-toluene sulfonic acid chloride, by reaction with 4-nitrophenol.

The dinitro compounds on which the diamines used for the phosgenation process of the present invention are based may also be obtained, for example, by condensation of α,ω-dihalogen alkanes ("halogen" meaning chlorine or bromine) with mixtures of alkali-4-nitrophenolate and alkali-4-nitro-3-methyl phenolate or by condensation of α,ω-alkane diols with mixtures of 4-nitrohalogen benzene and 2-nitro-5-halogen toluene in the presence of bases. Depending upon the product ratio used, statistical mixtures which, in addition to the α-(4-nitrophenoxy)-ω-(4-nitro-3-methylphenoxy)-alkanes, also contain bis-(4-nitrophenoxy)alkanes and bis-(4-nitro-3-methylphenoxy)-alkanes are obtained. If desired, the pure dinitro compounds corresponding to the diamine represented by formula (IV) may be isolated from the mixtures accumulating, for example by fractional crystallization. It would also be possible to isolate the pure diamines corresponding to formula (IV) by distillation of the diamine mixture produced by hydrogenation of the mixture of dinitro compounds. It would also be possible in principle to isolate the isocyanate represented by formula (I) in pure form by distillation of the diisocyanate mixture obtained by phosgenation of the diamine mixture. The mixtures of dinitro compounds need not however be separated into individual components. They may advantageously be processed as such to the corresponding diamie mixtures and in turn to the diisocyanate mixtures of the present invention.

It is possible in this way to obtain particularly interesting diisocyanate mixtures of which (a) at least 30 wt. %, preferably 30 to 50 wt. % and more preferably 35 to 50 wt. % are diisocyanates corresponding to the formula

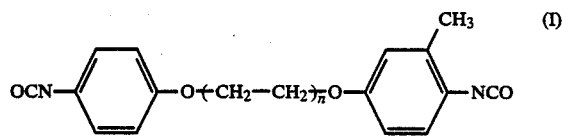

(b) up to 50 wt. %, preferably 5 to 45 wt. % and more preferably 10 to 35 wt. % are diisocyanates corresponding to the formula

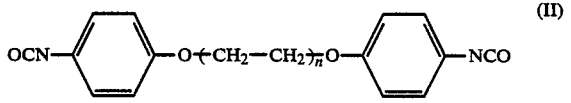

and (c) up to 50 wt. %, preferably 5 to 45 wt. % and more preferably 10 to 35 wt. % are diisocyanates corresponding to the formula

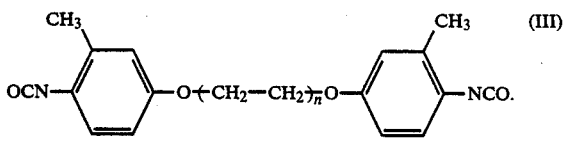

The percentages indicated add up to 100 in each case. An "asymmetrical" distribution within the ranges mentioned may also be present in these mixtures. For example, where correspondingly different quantities of 4-nitrohalogen-benzene and 2-nitro-5-halogentoluene are used for the preparation of the dinitro compounds, an asymmetrical distribution will result. The quantitative composition of the diisocyanate mixtures of the present invention corresponds very closely to the quantitative composition of the diamine mixtures on which they are based and of the mixtures of dinitro compounds on which the mixtures of the diamines are based. Accordingly, the composition of the diisocyanate mixtures of the present invention may readily be adjusted through suitable choice of the quantitative ratios of the mononitro compounds from which they are produced.

The diamines or diamine mixtures to be phosgenated in accordance with the present invention may be used in the technical purity in which they accumulate during their production or in purified form. Purification may be carried out, for example, by dissolution in dimethyl formamide and subsequent precipitation with water or by distillation.

The diamines or diamine mixtures may be used either as such or in the form of their adducts with hydrogen chloride or with carbon dioxide. In other respects, the phosgenation is carried out by methods known to those skilled in the art. Such processes are described, for example, in Liebigs Annalen der Chemie, Vol. 562, 1949, pages 75 to 109, in Ullmanns Encylopadie der Technischen Chemie, Vol. 14, 4th Edition, 1977, pages 350 to 354 or in Houben-Weyl, Methoden der Organischen Chemie, Vol. E4, 4th Edition, 1983, pages 741 to 753.

The phosgenation reaction may be carried out continuously or in batches, preferably in the presence an inert solvent. Suitable solvents include the solvents normally used for phosgenation processes, such as aliphatic, cycloaliphatic or aromatic hydrocarbons, halogenated hydrocarbons, nitro hydrocarbons, aliphatic-aromatic ethers, aromatic ethers, carboxylic acid esters, carboxylic acid nitriles, sulfones, phosphoric acid halides and phosphoric acid esters. Examples of suitable solvents include: trimethyl pentane, decahydronaphthalene, toluene, 1, 2-dichloroethane, chlorobenzene, chlorotoluene, 1, 2-dichlorobenzene, nitrobenzene, anisole, phenetol, diphenyl ether, butyl acetate, tetramethylene sulfone, phosphorus oxychloride and phosphoric acid trimethyl ester. Technical chlorobenzene or technical 1,2-dichlorobenzene is preferably used as solvent. It is of course also possible to use mixtures of such solvents. The diisocyanates of the present invention show only low solubility at low temperatures in most of the solvents mentioned above.

In the practical application of the phosgenation process of the present invention, the solvents named above all act as a suspending agent for the diamine or its hydrogen chloride or carbon dioxide adducts at the low phosgenation temperatures. They act as a genuine solvent for the starting material at higher temperatures and the diisocyanate product of the process.

The mixtures of starting materials to be phosgenated and solvent used in the practice of the present invention are generally "solution suspensions" containing approximately 2 to 70 wt. % of diamine or diamine adduct. The expression "solution suspension" is intended to indicate that the starting materials are present partly in dissolved form and partly in suspended form, particularly where the diamines are used, as is preferably the case.

The phosgenation reaction may be carried out, for example, in two stages on the known principle of "cold-hot phosgenation" or in one stage on the principle of "hot phosgenation". In "cold-hot phosgenation", the reaction of the starting material to be phosgenated takes place generally at $-20°$ to $+40°$ C. and preferably at $-10°$ to $+30°$ C. at the beginning of the reaction and the subsequent hot phosgenation at $40°$ to $260°$ C. and preferably at $80°$ to $220°$ C. In this "cold-hot phosgenation", the reaction mixture may be heated uniformly or in steps between the starting temperature and the elevated temperature.

In "hot phosgenation", the starting material to be phosgenated comes into contact with the phosgene immediately at temperatures of from $40°$ to $260°$ C. and preferably at temperatures of from $80°$ to $220°$ C.

"Cold-hot phosgenation" is the preferred procedure for phosgenation of the diamine (instead of the hydrogen chloride or carbon dioxide adducts). In this case, no significant reaction between the suspended diamine and the phosgene added takes place at the low temperatures mentioned. It is only during the subsequent increase in temperature that the diamine begins to react with the phosgene as its solubility increases.

Phosgenation is preferably carried out at normal pressure or under elevated pressure. The reaction pressure is generally in the range of from 0.9 to 100 bar and preferably in the range of from 1 to 60 bar.

The starting material to be phosgenated is generally combined with 1 to 10 times and preferably with from 1.05 to 6 times the stoichiometric quantity of phosgene. The phosgene may be introduced into the reaction mixture either all at once or in portions. It may be advantageous (for example, where the process is carried out in batches) to initially introduce only part of the quantity of phosgene to be used into the reaction mixture and then to introduce the remainder into the reaction mixture in further portions or continuously over a relatively long period.

The phosgenation of the diamines in accordance with the present invention may be accelerated by the addition of catalyst (for example, dimethyl formamide) and/or acid acceptors (for example, pyridine). In general, however, the reaction velocities during phosgenation of the diamine are sufficient in the absence of such a catalyst.

The reaction time for the phosgenation reaction depends upon the reaction conditions applied and, in particular, upon the reaction temperatures, the phosgene excess, the dilution with solvent and any catalyst(s) and/or acid acceptor(s) added.

On completion of the phosgenation reaction, the reaction mixture is worked up in known manner by separating off gaseous constituents (hydrogen chloride, excess phosgene) and removing the solvent by distillation. Before the solvent is removed by distillation, any solid secondary products present may be removed by filtration or centrifuging. If desired, the crude product accumulating as distillation residue after removal of the solvent by distillation may be purified by recrystallization from a suitable inert solvent, for example toluene, or preferably by distillation.

Although the diisocyanates of the present invention are heat-stable substances, it may be advisable to carry out purification of the diisocyanates by distillation in the absence of significant temperature stressing, for example in a thin-layer evaporator. If desired, the diisocyanates may be freed from troublesome secondary products (for example, thermolabile chlorine-containing compounds) after their purification by heating at temperatures of from 160° to 250° C. and preferably at temperatures of from 180° to 230° C.

The new diisocyanates or diisocyanate mixtures of the present invention may be used for the production of polyurethane plastics, particularly solid or cellular polyurethane elastomers instead of the known diisocyanates used for this purpose (See, for example, the literature references cited above or even "Kunststoff-Handbuch", Vol. VII, "Polyurethane" by Vieweg and Hochtlen, Carl Hanser Verlag Munich (1966), more especially pages 206–297).

In addition to the diisocyanate mixtures obtained by phosgenating mixtures of diamines, corresponding mixtures which have been obtained by mixing a pure monomethyl-substituted diisocyanate separately prepared with separately prepared diisocyanates containing no methyl substituents and/or two methyl substituents may also be used to produce polyurethanes in accordance with the present invention. Where mixtures of pre-prepared diisocyanates are used, mixtures which contain only one of components b) or c) in addition to the compulsory component a) of the mixtures of the present invention may of course also be used. The diisocyanates or diisocyanate mixtures of the present invention may of course also be used in admixture with other known polyisocyanates as starting materials for the production of polyurethane plastics by the known polyaddition process.

Polyurethanes, particularly polyurethane elastomers are preferably produced by reacting a diisocyanate of the present invention (formula (I)) or using a diisocyanate mixture according to the present invention (components a), b) and c)) with a hydroxyl group-containing material, preferably difunctional and/or trifunctional polyhydroxyl compounds having a molecular weight of from 400 to 10,000 and preferably of from 800 to 3,000, more preferably polyhydroxyl polyesters or polyhydroxyl polyethers, a chain extending agent having a molecular weight of from 60 to 399 (i.e. compounds containing alcoholic hydroxyl groups or primary or secondary amino groups and having a functionality of 2 in the context of the isocyanate addition reaction), optionally in the presence of other auxiliaries and additives known to those skilled in the chemistry of polyurethane elastomers.

The polyaddition reaction may be carried out by the known prepolymer process by reaction of the diisocyanate component with a difunctional and/or trifunctional polyhydroxyl compound at an equivalent ratio of isocyanate groups to isocyanate-reactive groups of greater than 1.3:1, and subsequent reaction of the NCO prepolymer thus obtained with a chain extending agent. The polyaddition reaction may also be carried out in one step by reaction of the diisocyanate component with a mixture of polyhydroxyl compound(s) and chain extending agent. In both variants, the equivalent ratio of isocyanate groups to the total quantity of isocyanate-reactive groups is generally from 0.8:1 to 1.3:1 and preferably from 0.95:1 to 1.1:1. The temperatures at which these reactions are carried out are generally in the range from 60° to 180° C. and preferably in the range from 80° to 150° C. The reactions may be carried out in the presence or absence of suitable inert solvents.

The polyurethane plastics, more especially polyurethane elastomers, prepared with the diisocyanates (component a)) or diisocyanate mixtures (components a), b), and c)), of the present invention may be solid or cellular products. The production of both types of polyurethane elastomers is carried out by known methods (See, for example, the Vieweg et al reference). For example, the production of cellular polyurethane elastomers may be carried out using water as sole chain-extending agent or as co-chain-extending agent.

The plastics, more especially elastomers, prepared with the diisocyanates (component (a)) or diisocyanate mixtures (components (a), (b) and (c)) of the present invention show outstanding mechanical and thermal properties. They are therefore eminently suitable for spring and shock-absorbing elements, buffers, wheel coverings, seals, shoe soles and similar applications where the material is exposed to severe mechanical and thermal stressing.

The invention is further illustrated but is not intended to be limited by the following examples in which all parts and percentages are by weight unless otherwise specified.

EXAMPLES

EXAMPLE 1

(1a) Preparation of 4-toluene sulfonic acid-[2-(4-nitro phenoxy)-ethyl]-ester

A solution of 915 g 2-(4-nitrophenoxy)-ethanol in 1 liter chloroform was introduced into a 6 liter flask, followed by the addition of 950 g of 4-toluene sulfonic acid chloride. The mixture was cooled with stirring to 0° C. 790 g pyridine were added dropwise to the mixture over a period of 3 hours with stirring and cooling at 0° to 3° C. Thereafter the reaction mixture was stirred for 2 hours at room temperature and then introduced into a mixture of 4 kg ice and 1.4 liter concentrated hydrochloric acid. After addition of 2 liters chloroform, the organic phase was separated off in a separation funnel, washed twice with 2 liters water and completely concentrated in vacuo. The crystalline crude product remaining behind was recrystallized from ethyl acetate and produced 1466 g (87% of the theoretical) of crystals melting at 121° C. $C_{15}H_{15}NO_6S$ (337.4)

(1b) Preparation of 1-(4-nitrophenoxy)-2-(4-nitro-3 methyl-phenoxy)-ethane 6 liters of ethylene glycol were introduced into a 10 liter flask, followed by the addition with stirring of 760 g of a 30% solution of sodium methylate in methanol and then 612 g 4-nitro-3-methyl phenol. Methanol was then distilled off from the mixture at 80° C., the pressure being reduced so that the head temperature was 40° to 50° C. 1348 g 4-toluene sulfonic acid-[2-(4-nitrophenoxy)-ethyl]-ester were then added to the reaction mixture in portions at 80° C., followed by stirring for 6 hours at 100° C. After cooling to room temperature, the mixture was stirred into 14 liters water. The precipitated crystals were filtered off under suction and washed twice with 1 liter water, then twice with 1.5 liters 5% sodium hydroxide, twice more with 1 liter water and, finally, with 1 liter methanol. After drying, the crystals were recrystallized from ethyl acetate, 1029 g (81% of the theoretical) of pure product being obtained.

$C_{15}H_{14}N_2O_6$ (318.3)

C calc. 56.6%; found 56.4%;

H calc. 4.4%; found 4.4%;

N calc. 8.8%; found 8.8%.

(1c) Preparation of 1-(4-aminophenoxy)-2-(4-amino-3-methylphenoxy)-ethane.

A solution of 1400 g 1-(4-nitrophenoxy)-2-(4-nitro-3-methylphenoxy)-ethane in 7 liters dimethyl formamide was initially introduced into a hydrogenation autoclave and, after the addition of Raney nickel, was reacted while stirring by introducing hydrogen under pressure. The hydrogenation reaction was carried out for 2 hours at 75° C. and then for 1 hour at 90° C. under a pressure of 40 to 50 bar. The autoclave was then vented, the hot reaction mixture was removed and the catalyst was separated off by filtration. The reaction solution was completely concentrated in vacuo and the crude product remaining behind was recrystallized twice from isopropanol. 1041 g (92% of the theoretical) of crystals melting at 104° C. were obtained.

$C_{15}H_{18}N_2O_2$ (258.3)

C calc. 69.7%; found 69.2%.

H calc. 7.0%; found 7.0%

N calc. 10.8%; found 10.5%

(1d) Production of 1-(4-isocyanatophenoxy)-2-(4-iso cyanato-3-methylphenoxy)-ethane A solution of 350 g phosgene in 3.8 liters anhydrous chlorobenzene was introduced into a 6 liter laboratory phosgenation reactor, followed by the addition at 0° to 10° C. of 387 g 1-(4-aminophenoxy)-2-(4-amino-3-methylphenoxy)-ethane. While more phosgene (40 to 50 g/h) was introduced, the mixture was rapidly heated to 60° C. and then over a period of 2.5 hours to reflux temperature. After another hour's phosgenation under reflux, a clear solution had formed. The reaction mixture was freed from excess phosgene and from the solvent by distillation. The crude product remaining behind was purified by distillation in vacuo. The diisocyanate distilled over without any first runnings at 196° to 198° C./0.5 mbar in the form of a colorless liquid which rapidly solidified into crystals melting at 86° to 87° C. Yield: 446 g (96% of the theoretical).

$C_{17}H_{14}N_2O_4$ (310.3)

NCO content: calc. 27.1% found 27.0%.

The diisocyanate could be redistilled with virtually no residue and gave colorless crystals of unchanged melting point containing 70 ppm hydrolyzable chlorine.

EXAMPLE 2

(Preparation of a mixture of 1,2-bis-(4-isocyanatophenoxy)-ethane, 1-4-isocyanatophenoxy)-2-(4-isocyanato-3-methylphenoxy)-ethane and 1,2-bis-(4-isocyanato-3-methylphenoxy)-ethane) (2a) Preparation of a mixture of the corresponding dinitro compounds A mixture of 4.5 liters ethylene glycol, 1749 g aqueous 4-nitro-3-methyl phenol (67.0%) and 1080 g aqueous 4-nitrophenol (98.6%) was introduced into a 10 liter flask equipped with a reflux condenser, followed by the addition with stirring of 1226 g 50% sodium hydroxide and 162 g anhydrous soda. The mixture was freed from water by distillation in a water jet vacuum at 100° to 110° C., after which 757 g 1,2-dichloroethane were added dropwise under normal pressure and gentle reflux over a period of about 3 hours at 110° to 120° C. Thereafter the reaction mixture was heated to 130 C. and further 152 g 1,2-dichloroethane were added dropwise under gentle reflux over a period of about 1 hour at 130° to 140° C. The mixture was stirred for 4 hours at 140° C. and then cooled to room temperature. The precipitated crystals were filtered off under suction, briefly boiled with vigorous stirring in 5 liters water, filtered under suction again after cooling, washed with 5 liters water and then with 1 liter methanol and, finally, dried in vacuo at 70° C. 2238 g pale brownish crystals melting at 169° to 177° C. were obtained.

(2b) Preparation of a mixture of the corresponding diamines 6 liters dimethyl formamide and 1900 g of the mixture prepared in Example 2a were initially introduced into a hydrogenation autoclave and, after the addition of Raney nickel, were reacted with stirring by introducing nitrogen under pressure at 40 to 50 bar. Hydrogenation was carried out for 2 hours at 75° C. and then for 1 hour at 90° C. The autoclave was then vented, the hot reaction mixture was removed and the catalyst was separated off by filtration. The reaction solution was completely concentrated in vacuo. 1448 g of a crystalline product melting at 81° to 85° C. remained behind.

(2c) Preparation of the diisocyanate mixture

A solution of 350 g phosgene in 3.8 liters anhydrous chlorobenzene was initially introduced into a 6 liter laboratory phosgenation reactor, followed by the addition at 0° to 10° C. of 380 g of the diamine mixture prepared in Example 2b). While more phosgene (40 to 50 g/h) was introduced, the mixture was rapidly heated to 60° C. and then over a period of 2.5 hours to reflux temperature. After another hour's phosgenation under reflux, a clear solution had formed. The reaction mixture was freed from the excess phosgene and from the solvent by distillation. The crude product remaining behind was purified by distillation in vacuo. The diisocyanate mixture distilled over without any first runnings at 194°–200° C./0.5 mbar in the form of a colorless liquid which slowly solidified into crystals. The product was almost completely redistilled, giving 424 g colorless crystals melting at 85° to 90° C.

For analysis, a representative sample of the diisocyanate mixture was converted into the corresponding diethyl urethane mixture by boiling for 1 hour in excess ethanol. The mixture was completely freed from ethanol by distillation and then analyzed by high-pressure liquid chromatography (HPLC) using an external standard. The diisocyanate was found by conversion to have the following composition: 24.8% 1,2-bis-(4-isocyanatophenoxy)-ethane, 49.9% 1-(4-isocyanatophenoxy)-2-(4-isocyanato-3-methylphenoxy)-ethane and 25.2% 1,2-bis-(4-isocyanato-3-methylphenoxy)-ethane. NCO content of the diisocyanate mixture: Calc. 27.1%; Found 26.9%.

EXAMPLE 3

(3a) The reaction was carried out in the same way as described in Example 2a) except that 1166 g 4-nitro-3methyl phenol (67.0%) and 1440 g 4-nitrophenol (98.6%) were used. 2165 g of a mixture of dinitro compounds in the form of brownish crystals melting at 150° to 155° C. were obtained.

(3b) 1900 g of the mixture prepared in Example 3a) were hydrogenated and worked up in the same way as described in Example 2b). 1438 g of a diamine mixture in the form of crystals melting at 82° to 89° C. were obtained.

3c) To prepare the diisocyanate mixture, 380 g of the diamine mixture prepared in Example 3b) were phosgenated and worked up in the same way as described in Example 2c). On distillation of the crude product, the mixture distilled over without any first runnings at 194°–203° C./0.5 mbar. Re-distillation gave 419 g colorless crystals melting at 76° to 80° C. Analysis of the mixture was carried out in the same way as described in Example 2c) and revealed the following composition: 43.1% 1,2-bis-(4-isocyanatophenoxy)-ethane, 45.1% 1-(4-isocyanatophenoxy)-2-(4-isocyanato-3-methylphenoxy)-ethane and 11.7% 1,2-bis-(4-isocyanato-3-methylphenoxy)-ethane.

NCO content of the diisocyanate mixture:
Calc 27.5%; found 27.2%.

EXAMPLE 4

(4a) The reaction was carried out in the same way as described in Example 2a) except that 2332 g 4-nitro-3methyl phenol (67.0%) and 720 g 4-nitrophenol (98.6%) were used. 2279 g of a mixture of dinitro compounds in the form of pale brownish crystals melting at 175°–178° C. were obtained.

(4b) 1900 g of the mixture prepared in Example 4a) were hydrogenated and worked up in the same way as described in Example 2b). 1454 g of a diamine mixture were obtained in the form of crystals melting at 87° to 90° C.

(4c) To prepare the diisocyanate mixture, 380 g of the diamine mixture prepared in Example 4b) were phosgenated and worked up in the same way as described in Example 2c). On distillation of the crude product, the mixture distilled over without any first runnings at 195°–199° C./0.4 mbar. Re-distillation gave 422 g colorless crystals melting at 90° to 100° C. Analysis of the mixture was carried out in the same way as described in Example 2c) and revealed the following composition: 10.3% 1,2-bis-(4-isocyanatophenoxy)-ethane, 42.5% 1-(4-isocyanatophenoxy)-2-(4-isocyanato-3-methylphenoxy)-ethane and 47.0% 1,2-bis-(4-isocyanato-3-methylphenoxy)-ethane. NCO content of the diisocyanate mixture: Calc. 26.6% found 26.6%

EXAMPLE 5

(Preparation of a mixture of 1,4-bis-(4-isocyanatophenoxy)-butane, 1-(4-isocyantophenoxy)-4-(4-isocyanato-3-methyl-phenoxy)-butane and 1,4-bis-(4-isocyanato-3-methylphenoxy)-butane)

(5a) The reaction was carried out in the same way as described in Example 2a), except that 1,4-dichlorobutane (first portion: 972 g, second portion: 98 g) was used instead of 1,2-dichloroethane and the reaction was carried out without reflux. 2306 g of a mixture of dinitro compounds were obtained in the form of brownish crystals melting at 88° to 94° C.

(5b) 1900 g of the mixture prepared in Example 5a) were hydrogenated and worked up in the same way as described in Example 2b). Removal of the solvent left 1417 g of a diamine mixture in the form of a brownish, viscous liquid.

(5c) To prepare the diisocyanate mixture, 420 g of the diamine mixture prepared in Example 5b) were phosgenated and worked up in the same way as described in Example 2c). On distillation of the crude product, the mixture distilled over without any first runnings at 174°–178° C./0.2 mbar. Re-distillation gave 413 g of a colorless liquid which solidified only slowly into crystals melting at 62° to 69° C. Analysis of the mixture carried out in the same way as described in Example 2c) revealed the following composition: 25.5% 1,4-bis(4-isocyanatophenoxy)-butane, 46.3% 1-(4-isocyanatophenoxy)-4-(4-isocyanato-3-methylphenoxy)-butane and 28.1% 1,4-bis-(4-isocyanato-3-methylphenoxy)-butane.

NCO content of the diisocyanate mixture:
Calc. 24.8%; found 25.1%.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A diisocyanate or diisocyanate mixture composed of
   (a) from 30 to 100 wt. % of diisocyanate corresponding to the formula

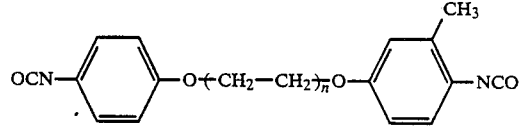

(b) from 0 to 50 wt. % of diisocyanate corresponding to the formula

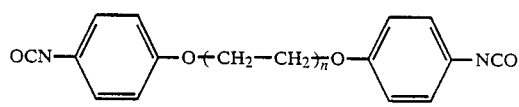

and (c) from 0 to 50 wt. % of diisocyanate corresponding to the formula

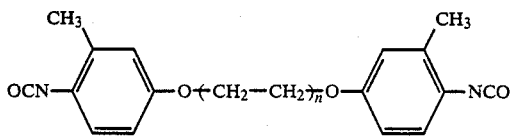

in which n has a value of 1, 2, or 3 and the percentages indicated add up to 100.

2. The diisocyanate of claim 1 in which component (a) is present in a quantity of from 30 to 50 wt. %, component (b) is present in a quantity of from 5 to 45 wt. % and component (c) is present in a quantity of from 5 to 45 wt. %.

3. The diisocyanate of claim 1 in which component (a) is present in a quantity of from 35 to 50 wt. %, component (b) is present in a quantity of from 10 to 35 wt. % and component (c) is present in a quantity of from 10 to 35 wt. %.

4. A process for producing the diisocyanate or diisocyanate mixture of claim 1 which comprises reacting with phosgene (a) a diamine corresponding to the formula

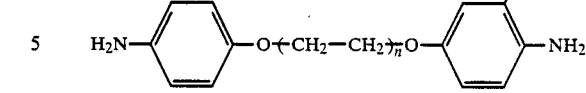

or mixtures thereof with one or more diamines selected from the group consisting of (b) a diamine corresponding to the formula

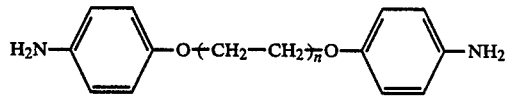

and (c) a diamine corresponding to the formula

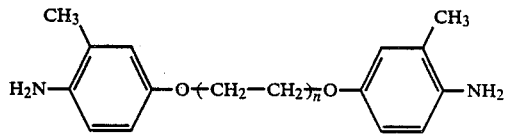

in which n is 1, 2 or 3, or adducts of said diamines with hydrogen chloride or carbon dioxide in which the quantitative composition is such that the diisocyanate produced therefrom will satisfy the composition requirements of (a), (b) and (c).

* * * * *